United States Patent [19]

Yang

[11] Patent Number: 4,877,739

[45] Date of Patent: Oct. 31, 1989

[54] ANTIAMMONIA AZOTOBACTER AND THE USE THEREOF

[76] Inventor: Zhen H. Yang, No. 101 Hu Dong Road, Fu Zhou City, Fu Jian Province, China

[21] Appl. No.: 252,578

[22] Filed: Sep. 30, 1988

Related U.S. Application Data

[62] Division of Ser. No. 913,431, Sep. 30, 1986, abandoned.

[30] Foreign Application Priority Data

Apr. 8, 1986 [CN] China .................................. 86100490

[51] Int. Cl.$^4$ ............................................. C12N 1/20
[52] U.S. Cl. .................................. 435/252.1; 435/243; 435/244; 435/831; 426/61; 426/635
[58] Field of Search ................ 435/253, 243, 244, 831

[56] References Cited

U.S. PATENT DOCUMENTS

| 3,423,289 | 1/1969 | Bulen | 435/831 |
| 3,560,344 | 2/1971 | Bulen | 435/831 |
| 4,234,688 | 11/1980 | Righelato | 435/831 |

*Primary Examiner*—Peter D. Rosenberg
*Attorney, Agent, or Firm*—Ladas & Parry

[57] ABSTRACT

This invention relates to a group of autogenic antiammonia azotobacter represented by 851 yellow. It can utilize low price starch medium. This culture fluid of azotobacter can be used for manufacturing single cell proteins rich in Se, Zn, $V_E$, $V_B$, $V_K$, anticancer and antiaging tonic medicines. It also can be used for manufacturing bacteria manure, eel and animal forage, additive, antiseptic and binder.

14 Claims, No Drawings

ANTIAMMONIA AZOTOBACTER AND THE USE THEREOF

This is a divisional of co-pending application Ser. No. 913,431, filed on Sept. 30, 1986, abandoned.

This invention relates to autogenic antiammonia azotobacter, especially a mutant strain, azotobacter, 851 yellow induced from Azotobacter vinelandii, 851 yellow, as inoculum in the industrial fermentation, can produce single cell protein riched in Se, Zn, vitamines and bacterial manure by utilization of the atmospheric nitrogen.

At present, scientists all over the world are studying the bio-azotofication. They hope that autogenic azotobacter will directly transform the atmospheric nitrogen into protein and fertilizer to ease the contradiction between the population and the food in the world today. Because the azotobacter in nature is not antiammonia azotobacter, it is of little value of spreading and applying.

The invention offers a group of azotobacters which have capability of anitammonia nitrogen-fixation, and have higher azotase activity. They can strongly fix the atmospheric nitrogen in the presence of the nitrogen-containing compound in the medium or the environment. In order to produce products which are valuable to industrial production such as single proteins containing Se, Zn, lots of vitamin C.D.K., vitamin E, bacterial manure and a series of products, the medium which is suitable for growth of the strain has been devised in this invention.

One of the strains according to this invention is the antiammonia azotobacter 851 yellow. It has remarkably the ability of antiammonia nitrogen-fixation. The strains were bred through breeding by artifical mutagenesis from Azotobacter vinlandii because of glutamine synthetase gene mutation. The difference between the mutant strain and its parents is that the former can keep higher azotase activity in the medium containing nitrogen, even in the presence of $(NH_4)_2SO_4$. (See Examples 1, 2, 3)

The strain can make use of starch directly. All substances that contain starch such as potato, sweet potato, corn etc. can be used as the carbon source for 851 yellow to grow. Using "851" yellow as productive inoculum, protein riched in Se and Zn single cell protein containing various vitamin can be produced in the starch culture medium according to this invention. In 100 ml of the culture fluid, the amount of the total amino acid is 0.2-2 g; organic seleninum, 0.5-5 ppm; Zn 5-20 ppm. In 100 ml of the culture fluid of this strain, the vitamin E is in an amount of 8.2-114 mg (results of laboratory), when it is incubatated n the mannitol yeast extract medium, and mannitol is used as carbon source. This strain is also suitable for producing the single cell protein containing vitamine by using the waste molasses as the carbon source. The amount of total amino acids in the culture fluid is 200-500 mg/100 ml.

The antiammonia azotobacter according to this invention has overcome the disadvantage that azotobacter can not strongly fix the atmospheric nitrogen in the presence of the compound nitrogen. Thus, this strain is not only the better strain for producing bacterial manure, but also the industral strain for producing the signle cell proteins riched in Se-, Zn- and containing various vitamines.

The media devised and employed are:

| 1. The starch medium | |
|---|---|
| dry starch | 1-2% |
| fresh substances containing starch (sweet potato, potato etc.) | 10-20% |
| or dry substances containing starch (corn etc.) | 1-10% |
| yeast extract | 0.04-0.08% |
| $K_2HPO_4$ | 0.05%0.1% |
| $MgSO_4$ | 0.02-0.04% |
| NaCl | 0.02-0.04% |
| $CaCO_3$ | 0.25-0.5% |
| sodium molybdate | 10-20 ppm |
| boric acid | 10-20 ppm |
| $Na_2SeO_3$ | 5-20 ppm |
| $ZnSO_4$ | 5-20 ppm |
| 2. The mannitol medium | |
| mannitol | 1% |
| $KH_2PO_4$ | 0.02% |
| $MgSO_4$ | 0.02% |
| NaCl | 0.02% |
| $CaSO_4$ | 0.02% |
| $CaCO_3$ | 0.25-0.5% |
| 3. The mannitol-yeast extract medium | |
| mannitol | 1% |
| yeast extract | 0.04% |
| $K_2HPO_4$ | 0.05% |
| $MgSO_4$ | 0.02% |
| NaCl | 0.02% |
| $CaCO_3$ | 0.25-0.5% |
| sodium molybdate | 5-10 ppm |
| boric acid | 5-10 ppm |
| 4. The waste molasses medium | |
| molasses | 2-3% |
| $CaCO_3$ | 0.25%-0.5% |
| sodium molybdate | 5-10 ppm |
| $FeSO_4$ | 5-10 ppm |

The antiammonia azotobacter, 851 yellow as the productive strain is incubated for 86-110 hrs. in the fermentation tank which contains the medium of starch (corn powder) (semi-continuous fermentation). Ventilating Amount: 1:0.6-1.2, Stirring speed 100-300 rpm, Culture Temperature 25°-30° C., At the end of incubation the total amount of amino acid is 0.5-1 g; organic Se, 5 ppm; Zn, 20 ppm and vitamin C, E, $B_1$, $B_2$, $B_{12}$, A, K, D and nicotinic acid etc. in 100 ml of the culture fluid. After the culture fluid is dried directly at 80° C. the amount of dry substances is 5-12%, in which the protein is up to 15-30%.

The Drosophila life of the test group doubled that of the control group when the culture fluid of antiammonia azotobacter ("851" culture fluid) produced by this method was fed to Drosophila. "851" culture fluid was fed to the chick since they were 5 days old. The chicken of test group were in good health without disease, and grew up faster.

The results of test of reducing the amount of the peroxilipid in the liver of mouse showed that there were substances of antiaging in the "851" culture fluid, and it has the equal effect to vitamin E, or/even better than latter. (See Example 5)

The results of test on the synthesis of several tissue proteins of white mouse showed that "851" culture fluid can promote the synthesis of protein. (See Example 6)

The results of the chemical caricinogenic test of the white mouse. (See Example 7) showed that "851" culture fluid had the effect of preventing cancers "851" culture fluid can inhibit and kill the cacer cells of white mouse and patients with cancer. (See Example 8)

"851" culture fluid can be used to produce many products, such as forage addative of various animalseel, prawn chicken, duck, pig etc. It not only increased the nutrition of forage, but also solved the problem of binding of forage (See Example 3, 4). The culture fluid can also be used as the additive and the antiseptic various food to make some kinds of healthful food, such as bisuit, candy, bread and drink. (See Example 4)

"851" culture fluid was utilized to make cosmetics drugs (the anticancer-longisting and nourishing injection, tablet, powder etc. prepared by extracting or tablet, pill, syrup's etc. prepared directly). This culture fluid can be used as the medium for other bacteria. It provided itself as the carbon and nitrogen source for other bacteria directly because of the symbiosis between it and yeast.

The part of the plants above ground and the root system of the test group were more vigorous with prolonged life after "851" culture fluid has poured on the plants as compared with the control's. (See Example 9).

The examples and references hereinafter will describe the invention in a more detailed manner while the invention is not limited thereto.

EXAMPLE 1

10 mg, 200 mg and 300 mg of $(NH_4)_2SO_4$ were separately added to 1000 ml of solid culture medium which containd 400 mg of yeast extract. Then culture medium containing different amount of $(NH_4)_2SO_4$ was separately put into the inoculative bottles. Each bottle contained 10 ml of the medium which was in the shape of oblique plane. A colony of inoculum was picked with inoculating needle and marked on the oblique plane. All cultures were incubated for 24 hr, at 36° C. Then nitrogenase activitys were determined with ethinyl reduction. The results were shown in the following table.

| amount of Nitrogen compound in 1000 ml medium | nitrogenase activity (n mole ethylene/bottle · hr.) |
|---|---|
| yeast extract, 400 mg + $(NH_4)_2SO_4$, 100 mg | 8004 |
| yeast extract, 400 mg + $(NH_4)_2SO_4$, 200 mg | 2425 |
| yest extract, 400 mg + $(NH_4)_2SO_4$, 300 mg | 690 |

Note: The number of bacteria in each bottle is $4.7 \times 10^{14}$.

EXAMPLE 2

Starch culture medium employed contains 5% of corn powder in which the amount of proteins is 10.63%. 60 liter of raw material was added into 100 liter fermentat tank and incubated. Culture medium contained corn powder, 3 kg; yeast extract, 24 g. These compound nitrogen in the medium had no effect upon nitrogen fixation of 851 yellow.

The data of "851" culture fluid in productive process were in tables below.

| The data of "851" culture fluid in productive process | | | | | | |
|---|---|---|---|---|---|---|
| | period of culture (hr) | | | | | |
| | 0 | 4 | 12 | 16 | 20 | 24 | 28 |
| Ph | | 7.0 | | 6.9 | | 6 | |
| Total sugar (%) | | 2.5 | | 1.25 | | 1.25 | |
| Reduce sugar (%) | | 1.25 | | 0.625 | | 0.625 | |
| Amino-nitrogen (mg/100 ml) | | 0 | | 0 | | 0 | |
| Tatal nitrogen (%) | | 0.045 | | 0.036 | | | |
| Number of bacteria/ml | | $8 \times 10^9$ | | $4 \times 10^{12}$ | $20 \times 10^{12}$ | $8 \times 10^{14}$ | $8 \times 10^{16}$ |
| Nitrogenase activity (n mole enthylene/2 ml · hr.) | 63 | | 2144 | 522 | 5711 | 10804 | 40206 |

| | period of culture (hr) | | | | | |
|---|---|---|---|---|---|---|
| | 32 | 36 | 40 | 44 | 48 | 52 |
| Ph | 7 | | 7 | | 7.6 | |
| Total sugar (%) | 1.25 | | 4.25 | | 7.5 | |
| Reduce sugar (%) | 0.625 | | 0.34 | | 0.14 | |
| Amino-nitrogen (mg/100 ml) | | | 4.2 | | 4.2 | |
| Tatal nitrogen (%) | 0.073 | 0.075 | 0.086 | | | |
| Number of bacteria/ml | $20 \times 10^{16}$ | $32 \times 10^{18}$ | $16 \times 10^{18}$ | $12 \times 10^{19}$ | $8 \times 10^{20}$ | |
| Nitrogenase activity (n mole enthylene/2 ml | 11286 | 14596 | 19343 | 11645 | 26002 | 19812 |

| | period of culture (hr) | | | | | |
|---|---|---|---|---|---|---|
| | 56 | 64 | 76 | 88 | 100 | 112 |
| Ph | 7.0 | 7.0 | 7.0 | | | |
| Total sugar (%) | 3.13 | 2.5 | 0.312 | 2.5 | 1.25 | |
| Reduce sugar (%) | 0.1 | 0.12 | 0.09 | 0.11 | 0.09 | |
| Amino nitrogen (mg/100 ml) | 7.0 | 6.3 | 5.6 | 4.2 | 5.6 | |
| Tatal nitrogen (%) | | 0.11 | | | | 0.12 |
| Number of bacteria/ml | | | | | | |
| Nitrogenase activity (n mole enthylene/2 ml · hr.) | 8816 | | | | | |

The above table shows that the antiamonia azotobacter can strongly fix the atmospheric nitrogen in the fermment tank. After incubation for 112 hours, in the culture fluid there was 7 g of dry substances in which nitrogen was 3.99% and proteins was 25%.

EXAMPLE 3

851 anti ammonia azotobacter was incubated on a rotary shaker for 24 hr before it was inoculated to 60 liter of raw material in fermentation tank of 100 liter. The amount of inoculum was 3.2 liter. Its nitrogenase activity was 52492 n mole enthylene/2 ml.hr. after incubation for 33 hr. 60 liter of culture fluid was inculated to 1 ton of raw material in 2 ton fermentation tank. Just after inoculating, the nitrogenase activity was 521.2 nmole enthylene/2 ml.hr. After 12 hr of incubation, the nitrogenase activity was 3715 n mole enthylene/2 ml.hr. After 18 hr of incubation, the nitrogenase activity was 5344 n mole enthylene/2 ml.hr. Then the culture fluid in 2 ton tank was transfered to 20 ton fermentation tank in which 5 ton of raw material was prepared. The nitrogenase activities of culture fluid in 20 ton air-hoisty fermetation tank were determined with results in the table below.

| Nitrogenase activities of "851" yellow in 20 ton fermentation tank | | | | | | | | | | | | | | | |
|---|---|---|---|---|---|---|---|---|---|---|---|---|---|---|---|
| | period of culture hr. | | | | | | | | | | | | | | |
| | 4 | 8 | 12 | 16 | 20 | 24 | 28 | 32 | 36 | 40 | 44 | 48 | 56 | 60 | 64 |
| nitrogenase activities n molo. Enthylene 2 ml · hr. | 67 | 124 | 449 | 2942 | 6743 | 7491 | 22232 | 26752 | 18184 | 5016 | 8566 | 8630 | 5046 | 5066 | 4772 |

The starch medium employed in production contained 5% of corn, 0.04% of yeast extract. If differed from Example 2 by adding 0.5% of glucose. Thus, different products occured. After incubation for 64 hours, culture fluid was in the shape of colloid-solid which consisted of B-hydroxybutyric acid and polysaccharide etc. When heating, it is dissolved, but at the normal temperature, it also took the shape of colloid-solid. When it was immersed in warm water for 30 hr, it remained in good shape without putrid. This solloid-solid culture fluid can be added to common eel forage to prepare a new type of colloidal forage. This new forage can be fed directly, reduced production cost and saved labour.

EXAMPLE 4

5% of soybeen cake powder, 20% of fresh sweet potato were separatly used as medium to make trial production. The precipitate of culture fluid obtained was directly dried in far-infrared rays, then the amount of each amino- acids was determined with the acid hydrolysis method. The results are in the table below.

| a.a. | dry substances of 851 culture fluid of soybean cake powder % 86602 | dry substances of 851 sweet potato culture fluid % 86608 |
|---|---|---|
| aspartate | 5.3667 | 1.976 |
| threonine | 2.8352 | 0.9826 |
| serine | 2.2055 | 0.7854 |
| glutamic acid | 6.6705 | 2.3929 |
| proline | 1.8177 | 0.6708 |
| glucine | 2.8808 | 1.0712 |
| alanine | 4.2791 | 1.4937 |
| cystine | 0.2301 | 0.2801 |
| valine | 3.1889 | 1.2550 |
| methionine | 0.9191 | 0.1765 |
| isoleucine | 2.8086 | 0.8444 |
| leucine | 4.5656 | 1.4661 |
| Tyrosine | 1.9672 | 0.8977 |
| phenylalanine | 2.0808 | 2.9179 |
| lysine | 2.8078 | 0.8640 |
| Tryptophon | 0.0856 | 0.0908 |
| Histidine | 1.0669 | 0.3535 |
| arginine | 3.0449 | 0.9265 |
| total amount of amino acid | 48,817 | 19,4451 |

The above results showed that although the culture fluid was hydrolysed by the acid, Tryptophon can be detected, thesefore, the amount of Tryptophon is considerable in the "851" culture fluid, otherwise it can be undetected.

"851" yellow, antiammino nitrogen fixation bacteria grew very well in the medium of soybean cake powder. The strain can decomposite proteins of leguminous crops and make culture fluid release fishy odour. It can be used to develop dorado oil, artifical dried fish floss etc. The orange biscuit made with 14.5 kg of sweet potato culture fluid instead of eggs in which contained 8% of culture fluid. Its amount of each amino acid was just a little higher than the orange biscuit made with eggs without culture fluid (See the table below).

| | orange biscuit | |
|---|---|---|
| | +eggs % | +851 % |
| aspartate | 0.4498 | 0.5442 |
| threonine | 0.2966 | 0.3362 |
| serine | 0.4797 | 0.5612 |
| glutamic acid | 3.7541 | 3.9557 |
| proline | 1.2465 | 1.1757 |
| glycine | 0.4404 | 0.4163 |
| alanine | 0.4096 | 0.3692 |
| cystine | 0.3360 | 0.2778 |
| valine | 0.5242 | 0.5959 |
| methionine | 0.0756 | 0.1599 |
| isoleucine | 0.3418 | 0.4594 |
| leucine | 0.6923 | 0.7661 |
| Tyrosine | 0.6507 | 0.6464 |
| phenylalanine | 1.4949 | 1.3174 |
| lysine | 0.4328 | 0.4654 |
| Tryptophon | | |
| Histidine | 0.2312 | 0.2358 |
| arginine | 0.4130 | 0.4536 |
| total amount of amino acid | 12.2701 | 12.7367 |

Yellowish soft candy made with the "851" mannitol culture fluid adding agar, sugar and flavouring essence are sweet, crisp and refreshing.

Brown soft candy made with the "851" sweet potato culture fluid adding agar, sugar and flavouring essence have a unique style of taste.

Various type of cool cakes can be prepared with colloid corn powder culture fluid produced through adding 0.5% glucose and with sweet potato culture fluid, adjusting directly the colour, flavour and taste without using agar.

EXAMPLE 5

In order to distinguish the effect of 851 culture fluid on antiaging, the test of peroxidlipid of mouse liver was carried on in vivo. The results were in the following table.

| Group | Vit. E deficience | Complement Vit. E | "851" mannitol culture fluid. |
|---|---|---|---|
| numbers results | 16 | 18 | *18 |
| g liver (M ± S.d) | 378.2 ± 244.1 | 161.2 ± 17.2 | 140.2 ± 28.2 |

Compared with vit. E deficiency group   P < 0.01.
*p < 0.001.
compared with the 851 mannitol culture fluid   P < 0.02.

The results showed that in Both vit. E group and "851" mannitol culture fluid group, the amount of malonic aldehyde—products of Liver lipid peroxidation, decreased one half or more. The effect of "851" mannitol culture fluid was better than vit. E.

Note:
1. The amount of vit. E complemented was 100 mg/kg. food. Since the day before two days when the white mouse was attacted by carbon tetrachloride, Vit. E 40 mg/kg. body, weight, was complemented in intramuscular injection daily.
2. The mouse drink freely "851" mannitol culture fluid instead of water, in the meanwhile, 2 ml of "851" culture fluid was added to one mouse' forage daily.
3. In order to induce superfunction lipid peroxide state, on the day when feeding test carried on for 12 days, 150 1/kg. body weight, of carbon tetrachtoride was injected into mouse abdominal cavity. In 16 hours the liver was taken and assayed according to 1979 Hlrosh' ohkana el. method.

In order to distinguish the effect of 851 culture fluid on antiaging the test on serum peroxide lipid was carried on in human body, the results were in the table bellow.

The change of Amount of serum peroxide lipid in body after taking "851" products

| | | item | |
|---|---|---|---|
| | | Serum MDA n mole/ml (M ± S.d) | |
| Group | number (human) | before taking | after taking |
| taking "851" products | 22 | 3.25 ± 1.04 | 1.76 ± 0.66* |
| Control | 21 | 2.27 ± 1.20 | 2.19 ± 0.9 |

Compared after taking group with before taking group *P 0.001.

Notes:
1. This test was carried on in a sanatorium, so all testee took same diet, ceased to take hypoblood fat agent, antioxidant (Vit. E, Vit, C). etc.
2. The testee taking "851" products had 20 pieces of "851" biscuit, 10 pieces of "851" soft candy daily. The course of treatment casted 8-12 days.
3. "851" busicuit contains 8% "851" culture fluid, and '851' soft candy contains 30% "851" culture fluid.

The results above showed that "851" culture fluid products regularly taken as non-staple food significantly decreased the amount of lipid peroxide in human serum (MDA), and had great advantage of antiaging.

EXAMPLE 6

The "851" culture fluid can promote tissue proteins synthesis in liver, small intestine, serum and brain of mice, Results were shown in the following tables.

TABLE 1

| | the effect of 851 culture on fluid incorporation of $^3H$—Tyrosin into duodenum protein of white mouse | | | |
|---|---|---|---|---|
| Group | I | II | III | IV |
| Numbers of example results | 15 | 15 | 16 | 15 |
| (cpm/mg) (m ± s.d) | 554.1 ± 46.4 | 586.6 ± 173.8 | 622.4 ± 106.8* | 542.2 ± 73.7 |

*Compare group III with group I, P < 0.05

TABLE 2

| | The effect of 851 culture fluid on incorporation of H—Tyrosin into liver protein of mice | | | |
|---|---|---|---|---|
| Group | I | II | III | IV |
| number of example RESULTS | 15 | 15 | 16 | 16 |
| (CPM/mg) (m ± S.d) | 151.2 ± 37.2 | 174.7 ± 30.1 | 191 ± 50* | 168 ± 24 |

*Compare group III with group I, P < 0.025

TABLE 3

| | The effect of 851 culture fluid on the concentration of serum protein of mice | | | |
|---|---|---|---|---|
| Group | I | II | III | IV |
| number of example results | 16 | 16 | 15 | 16 |
| (g/dl) | 7.81 ± 0.58 | 7.33 ± 0.69 | 7.53 ± 0.51 | 7.79 ± 0.75* |

*Compare group IV with group I. P < 0.025.

TABLE 4

| | The effect of 851 culture fluid on incorporation of $^3H$—Tyrosin into brain protein of white mouse | | | |
|---|---|---|---|---|
| Group | I | II | III | IV |
| number | 16 | | 16 | 16 |

TABLE 4-continued

The effect of 851 culture fluid on incorporation of $^3$H—Tyrosin into brain protein of white mouse

| Group | I | II | III | IV |
|---|---|---|---|---|
| of example results | | | | |
| (CPM/mg. protein) (M ± S.d) | 77.06 ± 19.59 | | 98.78 ± 22.25 | 90.57 ± 14.11 |

*Compared with group I, p < 0.01.
**Compared with group I, P < 0.05.

The table 4 showed that the "851" culture fluid had promoted brain protein synthesis of white mouse.

We concluded sumarily that the 851 culture fluid was of great advantage to synthesis various tissue proteins of animals.

Notes:

Group I: 3.5 g of granular forage/a mouse/day, drink water.

Group II: 3.5 g of granular forage containing 0.25 g of giseng/a mouse/day, drink water.

Group III: granualr forage Containing corn culture fluid, 3.5 g/a mouse/day, drink dilute culture fluid (1:1) instead of water.

Group IV: granular forage containing sweat potato culture fluid, 3.5 g/amouse/day, drink dilute culture fluid (1:1) instead of water.

Each white mouse in group III, IV drank 4 ml of the "851" culture fluid daily.

After the 851 culture fluid products as non-staple food were taken by human regularly, the level of total serum proteins and albumin tended to increase. But it was not significant statistically. But after "<8g%" group took the "851" culture fluid products, the total amount of serum proteins, compared to before treatment, rose significantly (P<0.025). This meant that the "851" culture fluid products can promote serum protein Synthesis, improve protein nutrition in dificiently condition of protein in body.

The effect of the "851" Culture Fluid products on the total amount of serum proteins in human body.

| Group | ≧8 g % | <8 g % |
|---|---|---|
| Before treatment | 8.13 ± 0.15% | 7.3 ± 0.44** |
| After treatment | 8.04 ± 0.45 | 7.88 ± 0.45 |
| number of example | 9 | 12 |

Compare before treatment with after treatment in the same group, **P < 0.025

EXAMPLE 7

The "851" corn culture fluid had a remarkable inhibition on the formation of lung cancer of mice mutated by urethane, deduced the numbers of focus of animals, relieved the symptom, was of great advantage of preventing cancer.

The effect of "851" culture fluid on the lung cancer of white mouse by Urethane

| Group | number of example | number of animal with cancer (incidence of cancer) | number of cancer | | |
|---|---|---|---|---|---|
| | | | Total number | average | cancer mice average |
| normal | 38 | 3 (7.9%) | 4 | ΔΔ 0.105 ± 0.383 | ΔΔ 1.333 ± 0.577 |
| carcininstation | 37 | 28 (75.7%) | 133 | 3.892 ± 5.572 | 5.143 ± 5.802 |
| carcininstation + "851" corn culture fluid | 29 | 19 (65.5%) | 44 | 1.586 ± 2.13 | Δ 2.421 ± 2.219 |

Compared with Carcininstation group. P < 0.05, P
Compared with Carcininstation group. P < 0.05, P < 0.001

The difference between the normal and the Carcinostatic on incidence of cancer and numbers of cancer was significant through the above table. The difference between the "851" culture fluid and the carcinonstatic group on the incidence of cancer was not significant. The number of cancer of '851' corn culture fluid was 44 which was only one-third of the carcinostatic group. The difference between averages of two groups was significant statistically. It showed that "851" corn culture fluid can deduce the lung cancer degree of mouse led by urethane

EXAMPLE 8

The supernate of "851" culture fluid can inhibit and kill various cancer cells.

For example, 85FFGC cell lines of gastric cancer was inhibited, and killed. The cells of test group employed over 10% of "851" supernate appeared as inhibition and killed for 24–72 hours.

EXAMPLE 9

The test of 851 yellow, antiammonia nitroen fixation bacteria as bacterial manure.

The test group was watered with "851" culture fluid three times, each time 100 ml. 15 g of soil was taken after watering for 24 hr and assayed. Nitrogenase activity was 38 n mole enthylene/15 g.hr. The control group was also watered with 100 ml of '851' culture fluid three time, each time 100 ml. 10 g of soil was assayed. Its nitrogenase activity was zero. (The Soil employed in test was sterillized in autoclave before).

The parts of corn above ground of the test group grew better than the control's. And the former root also developed better than the latter. This fluid can promote development of the root system of the plant.

The root system of test group developed better than the control's.

I claim:

1. A group of autogenic azotobacters mutated from Azotobacter vinelandii, having the capability of antiammonia nitrofixation, wherein said azotobacters fix atmospheric nitrogen and maintain azotase activity in a culture medium containing nitrogen and ammonium sulfate.

2. A strain of azotobacter according to claim 1, designated as 851 yellow, deposited in ATCC No. 53547 on Oct. 7, 1986.

3. The forage containing the culture fluid of the microorganism according to claim 1.

4. The forage containing the culture fluid of the microorganism according to claim 2.

5. The forage additive containing the culture fluid of the microorganism according to claim 1.

6. The forage additive containing the culture fluid of the microorganism according to claim 2.

7. The antiseptic containing the culture fluid of the microorganism according to claim 1.

8. The antiseptic containing the culture fluid of the microorganism according to claim 2.

9. The binder containing the culture fluid of the microorganism according to claim 1.

10. The binder containing the culture fluid of the microorganism according to claim 2.

11. The healthcare food containing the culture fluid of the microorganism according to claim 1.

12. The healthcare food containing the culture fluid of the microorganism according to claim 2.

13. The single-cell protein containing the culture fluid of the microorganism according to claim 1.

14. The single-cell protein containing the culture fluid of the microorganism according to claim 2.

* * * * *